United States Patent [19]
Cheng et al.

[11] Patent Number: 6,133,263
[45] Date of Patent: Oct. 17, 2000

[54] ENDOTHELIN ANTAGONISTS WITH ETHER-LINKED GROUPS

[75] Inventors: Xue-Min Cheng; Annette Marian Doherty, both of Ann Arbor; William Chester Patt, Chelsea; Joseph Thomas Repine, Ann Arbor, all of Mich.

[73] Assignee: Warner-Lambert Company, Morris Plains, N.J.

[21] Appl. No.: 09/117,649

[22] PCT Filed: Mar. 12, 1997

[86] PCT No.: PCT/US97/03930

§ 371 Date: Aug. 3, 1998

§ 102(e) Date: Aug. 3, 1998

[87] PCT Pub. No.: WO97/37986

PCT Pub. Date: Oct. 16, 1997

Related U.S. Application Data

[60] Provisional application No. 60/015,238, Apr. 10, 1996.

[51] Int. Cl.$^7$ ...................... A61K 31/365; A61K 31/535; C07D 407/02; C07D 413/14
[52] U.S. Cl. ...................... 514/233.8; 514/464; 514/465; 544/148; 544/377; 548/526; 549/313
[58] Field of Search ..................................... 544/148, 313; 514/233.8

[56] References Cited

U.S. PATENT DOCUMENTS 5,691,373  11/1997  Berryman et al. .

FOREIGN PATENT DOCUMENTS 0436189  10/1991  European Pat. Off. .

OTHER PUBLICATIONS

Arai et al., "Cloning and expression of a cDNA encoding an endothelin receptor", Nature, 1990, 348, 730–732.
Sakurai et al., "Cloning of a cDNA encoding a non–isopeptide–selective subtype of the endothelin receptor", Nature, 1990, 348, 732–735.
Lin et al., "Cloning and functional expression of a vascular smooth muscle endothelin 1 receptor", Proc. Natl. Acad. Sci. USA, 1991, 88, 3185–3189.
Sakamoto et al., "Cloning and functional expression of human cDNA for the $Et_B$ endothelin receptor", Biochem. Biophys. Res. Comm., 1991, 178:2, 656–663.
Hosoda et al., "Cloning and expression of human endothelin–1 receptor cDNA", FEBS Letters, 1991, 287:1/2, 23–26.
Takayanagi et al., "Presence of non–selective type of endothelin receptor on vascular endothelium and its linkage to vasodilation", FEBS Letters, 1991, 282:1, 103–106.
Panek et al., "Endothelin and structurally related analogs distinguish between endothelin receptor subtypes", Biochem. Biophys. Res. Comm., 1992, 183:2, 566–571.
Yasuda et al., "Circulating immunoreactive endothelin in ischemic heart disease", American Heart Journal, 1990, 119:4, 801–806.
Stewart et al., "Plasma endothelin in coronary venous blood from patients with either stable or unstable angina", Br. Heart J., 1991, 66, 7–9.
Stewart et al., "Elevated Endothelin–1 in Heart Failure and Loss of Normal Response to Postural Change", Circulation, 1992, 85, 510–517.
Lerman et al., "Plasma Endothelin Concentrations in Humans With End–Stage Heart Failure and After Heart Transplantation", JAAC, 1992, 20:4, 849–853.
Rodeheffer et al., "Circulating plasma endothelin correlates with the severity of congestive heart failure in humans", Am. J. Hypertension, 1991, 4:9A–10A.
Rodeheffer et al., "Increased Plasma Concentrations of Endothelin in Congestive Heart Failure in Humans", Mayo Clin. Proc., 1992, 67, 719–724.
Stewart et al., "Increased Plasma Endothelin–1 in the Early Hours of Acute Myocardial Infarction", JAAC, 1991, 18:1, 38–43.
Tomoda, "Plasma endothelin–1 in acute myocardial infarction with heart failure", American Heart Journal, 1993, 125, 667–672.
Ray et al., "Circulating endothelin in acute ischaemic syndromes", Br. Heart J., 1992, 67, 383–386.
Tsuji et al., "Plasma endothelin levels during myocardial ischemia and reperfusion", Life Sciences, 1991, 48, 1745–1749.
Liu et al., "Ischaemia causes externalization of endothelin–1 binding sites in rat cardiac membranes", Biochem. Biophys. Res. Comm., 1989, 164:3, 1220–1225.
Watanabe et al., "Endothelin in myocardial infarction", Nature, 1990, 344, 114.
Margulies et al., "Increased Endothelin in Experimental Heart Failure", Circulation, 1990, 82:6, 2226–2230.
Kiowski et al., "Evidence for endothelin–1–mediated vasoconstriction in severe chronic heart failure", Lancet, 1995, 346, 732–736.

(List continued on next page.)

*Primary Examiner*—Robert W. Ramsuer
*Attorney, Agent, or Firm*—Elizabeth M. Anderson

[57] ABSTRACT

Novel nonpeptide endothelin antagonists with ether-linked groups are described, as well as methods for the preparation and pharmaceutical compositions of the same, which are useful in treating atherosclerosis, restenosis, Raynaud's phenomenon, mild or severe congestive heart failure, cerebral ischemia, cerebral infarction, embolic stroke, cerebral vasospasm, subarachnoid hemorrhage, hemorrhagic stroke, diabetes, gastric ulceration and mucosal damage, ischemnic bowel disease, Chrohn's disease, essential or malignant hypertension, pulmonary hypertension, pulmonary hypertension after bypass, acute respiratory distress syndrome, chronic obstructive pulmonary diseases, male penile erectile dysfunction, cancer, especially malignant hemangicendothelioma or prostate cancer, myocardial infarction or ischemia, acute or chronic renal failure, renal ischemia, radiocontrast-induced nepbrotoxicity, endotoxic, septic, hemorrhagic shock, angina, preeclampsia, asthma, arhythmias, benign prostatic hyperplasia, and elevated levels of endothelin.

30 Claims, No Drawings

OTHER PUBLICATIONS

Kiowski et al., "Vasodilator Effects of the Endothelin–1 Receptor Antagonist Bosentan in Patients with Severe Chronic Heart Failure", *JACC,* 1995, special edition 296A, 779–1.

López–Farré et al., "A role for endothelin in the maintenance of post–ischaemic renal failure in the rat", *Journal of Physiology,* 1991, 444, 513–522.

Stockenhuber et al., "Plasma levels of endothelin in chronic renal failure and after renal transplantation: impact on hypertension and cyclosporin A–associated nephrotoxicity", *Clinical Science,* 1992, 82, 255–258.

Kon et al., "Glomerular Actions of Endothelin In Vivo", *J. Clin. Invest.,* 1989, 83, 1762–1767.

Ohno, "Effects of Endothelin–specific Antibodies and Endothelin in Spontaneously Hypertensive Rats", *J. Tokyo Women's Medical College,* 1991, 61:10–11, 951–959.

Mino et al., "Protective effect of a selective endothelin receptor antagonist, BQ–123, in ischemic acute renal failure in rats", *Eur. J. Pharmacol.,* 1992, 221, 77–83.

Benigni et al., "A specific endothelin subtype A receptor antagonist protects against injury in renal disease progression", *Kidney International,* 1993, 44, 440–444.

Pagotto et al., "Expression and Localization of Endothelin–1 and Endothelin Receptors in Human Meringiomas", *J. Clin. Invest.,* 1995, 96, 2017–2025.

Nakagawa et al., "Measurement of Immunoreactive Endothelin–1 in Plasma of a Patient with Malignant Hemangioendothelioma", *Japan J. Dermatol.,* 1990, 100, 1453–1456.

Nelson et al., "Identification of endothelin–1 in the pathophysiology of metastatic adenocarcinoma of the prostate", *Nature Medicine,* 1995, 1:9, 944–949.

Imajo et al., "Physiological and pharmacological characterization of endothelin in the canine and human prostate", abstract submitted to the Annual Meeting of the American Urological Association, Inc., 1996, Orlando, Florida.

Noguchi et al., "An endothelin($ET)_A$ receptor antagonist, BQ–123, blocks ET–1 induced bronchoconstriction and tracheal smooth muscle (TSM) contraction in allergic sheep", *Am. Rev. Respir. Dis.,* 1992, 145 (4 Part 2), A858.

Clark et al., "Plasma endothelin levels in preeclampsia: Elevation and correlation with uric acid levels and renal impairment", *Am. J. Obstet Gynecol.,* 1992, 166:3, 962–968.

Pittet et al., "Elevated Plasma Endothelin–1 Concentrations Are Associated with the Severity of Illness in Patients with Sepsis", *Ann. Surg.,* 1991, 213:3, 261–264.

Gandhi et al., "Endothelin, a Potent Peptide Agonist in the Liver", *J. Biol. Chem.,* 1990, 265:29, 17432–17435.

Collier et al., "Plasma Endothelinlike Immunoreactivity Levels in IDDM Patients With Microalbuminuria", *Diabetes Care,* 1992, 15:8, 1038–1040.

Mortensen et al., "Chronic Hypertension Produced by Infusion of Endothelin in Rats", *Hypertension,* 1990, 15, 729–733.

Mortensen et al., "The salt–dependency of endothelin–induced hypertension in conscious rats", *FASEB J.,* 1991, 5, A1105.

Bazil et al., "Hemodynamic effects of an endothelin (ET) receptor antagonist in three rat models of hypertension", *J. Hypertension,* 1992, 10(Suppl 4), S49.

Han et al.,"Cardiac and vascular actions of sarafotoxin S6b and endothelin–1", *Life Sciences,* 1990, 46:11, 767–775.

Stein et al., "The Discovery of Sulfonamide Endothelin Antagonists and the Development of the Orally Active $ET_A$ Antagonist 5-(Dimethylamino)–N–(3, 4–dimethyl–5–isoxazolyl)–1–napthalenesulfonamide", *J. Med. Chem.,* 1994, 37:3, 329–331.

Yoshibayashi et al., "Plasma Endothelin Concentration in Patients With Pulmonary Hypertension Associated with Congenital Heart Defects", *Circulation,* 1991, 84:6, 2280–2285.

Giad et al., "Expression of endothelin–1 in the lungs of patients with pulmonary hypertension", *N. Engl. J. Med.,* 1993, 328:24, 1732–1739.

Abraham et al., "A specific endothelin–1 antagonist blocks inhaled endothelin–1–induced bronchoconstriction in sheep", *J. Appl. Physiol.,* 1993, 74:5, 2537–2542.

Donahue et al., "Pulmonary Hypoxia Increases Endothelin–1 Gene Expression in Sheep", *J. Surg. Res.,* 1994, 57, 280–283.

Eddahibi et al., "Protection from pulmonary hypertension with an orally active endothelin receptor antagonist in hypoxic rats", *Am. J. Physiol.,* 1995, 268, H828–H835.

DiCarlo et al., "$ET_A$–receptor antagonist prevents and reverses chronic hypoxia–induced pulmonary hypertension in rat", *Am. J. Physiol.,* 1995, 269, L690–L697.

Chen et al., "Endothelin–receptor antagonist bosentan prevents and reverses hypoxic pulmonary hypertension in rats", *J. Appl. Physiol.,* 1995, 79:6, 2122–2131.

Ishikawa et al., "Elevated levels of plasma endothelin–1 in young patients with pulmonary hypertension caused by congenital heart disease are decreased after successful surgical repair", *J. Thorac. Cardiovasc. Surg.,* 1995, 110, 271–273.

Komai et al., "Increased plasma levels of endothelin–1 after cardiopulmonary bypass in patients with pulmonary hypertension and congenital heart disease", *J. Thorac. Cardiovasc. Surg.,* 1993, 106, 473–478.

Nikolov and Semkova, "Cerebrovascular and CNS Effects of Endothelins—Target for Pharmacological Modification?", *Drugs of Today,* 1992, 28:5, 303–310.

Patel et al., "Therapeutic Potential of Endothelin Receptor Antagonists in Experimental Stroke", *Journal of Cardiovascular Pharmacology,* 1995, 26(Suppl. 3), S412–S415.

Barone et al., "The Endothelin Receptor Antagonist SB 217242 Reduces Cerebral Focal Ischemic Brain Injury", *Journal of Cardiovascular Pharmacology,* 1995, 26(Suppl.3), S404–S407.

Torralbo et al., "Alterations in Renal Endothelin Production in Rats With Reduced Renal Mass", *Am. J. Kidney Dis.,* 1995, 25:6, 918–923.

Clozel et al., "Pathophysiological role of endothelin revealed by the first orally active endothelin receptor antagonist", *Nature,* 1993, 365, 759–761.

Brooks et al., "SB 203220: A Novel Angiotensin II Receptor Antagonist and Renoprotective Agent", *J. Pharmacol. Exp. Ther.,* 1995, 274:3, 1222–1227.

Oldroyd et al., "Bosentan, an Orally Active Endothelin Antagonist: Effect on the Renal Response to Contrast Media", *Radiology,* 1995, 196, 661–665.

Kusumoto et al., "Effects of a new endothelin antagonist, TAK–044, on post–ischemic acute renal failure in rats", *Life Sciences,* 1994, 55:4, 301–310.

Clozel and Watanabe, "BQ–123, a peptidic endothelin $ET_A$ receptor antagonist, prevents the early cerebral vasospasm following subarachnoid hemorrhage after intracisternal but not intravenous injection", *Life Sciences,* 1993, 52:9, 825–834.

Caner et al., "Reversal of subarachnoid hemorrhage–induced vasoconstriction using an endothelin receptor antagonist", *Cerebral Vasospasm,* 1993, 217–220.

Foley et al., "Reversal of Subarachnoid Hemorrhage–induced Vasoconstriction with an Endothelin Receptor Antagonist", *Neurosurgery,* 1994, 34:1, 108–113.

Nirei et al., "An endothelin $ET_A$ receptor antagonist, FR139317, ameliorates cerebral vasospasm in dogs", *Life Sciences,* 1993, 52:23, 1869–1874.

Itoh et al., "A novel endothelin $ET_A$ receptor antagonist, BQ–485, and its preventative effect on experimental cerebral vasospasm in dogs", *Biochem. Biophys. Res. Comm.,* 1993, 195:2, 969–975.

Roux et al., "Ro 47–0203, an New Endothelin Receptor Antagonist Reverses Chronic Vasospasm in Experimental Subarachnoid Hemorrhage", *Circulation,* 1993, 88:4 part 2, 0907.

Lerman et al., "Circulating and tissue endothelin immunoreactivity in advanced atherosclerosis", *New England J. Med.,* 1991, 325:14, 997–1001.

Kanno et al., "Endothelin–1 and Vasculitis", *J. Amer. Med. Assoc.,* 1990, 264, 2868.

Zamora et al., "Serum endothelin–1 concentrations and cold provocation in primary Raynaud's phenomenon", *Lancet,* 1990, 336, 1144–1147.

Tahara et al., "Circulating Immunoreactive Endothelin in Patients Undergoing Percutaneous Transluminal Coronary Angioplasty", *Metab. Clin. Exp.,* 1991, 40:12, 1235–1237.

Douglas et al., "A Role for Endogenous Endothelin–1 in Neointimal Formation After Rat Carotid Artery Balloon Angioplasty", *Circulation Research,* 1994, 75, 190–197.

Miura et al., "Ischemic Bowel Necrosis Induced by Endothelin–1: An Experimental Model in Rats", *Digestion,* 1991, 48, 163–172.

Masuda et al., "Effect of Intravascular ethanol on modulation of gastric mucosal integrity: possible role of endothelin–1", *Am. J. Physiol.,* 1992, 262, G785–G790.

Murch et al., "High endothelin–1 immunoreactivity in Crohn's disease and ulcerative colitis", *Lancet,* 1992, 339, 381–385.

Lazaratos et al., "Bosentan antagonizes the effects of endothelin–1 on rat gastric blood flow and mucosal integrity", *Life Sciences,* 1995, 56:9, PL 195–200.

Allen and Frame, "The condensation of certain gamma–ketonic esters with aromatic aldehydes", *Can. J. Research,* 1932, 6, 605–613.

Allen et al., "The condensation of certain gamma–ketonic esters with aromatic aldehydes. II", *Can. J. Research,* 1933, 8, 137–141.

Allen et al., "Certain reactions of gamma ketonic acids", *Can. J. Research,* 1934, 11, 382–394.

Allen et al., "a–Aryl–β–aroylpropionic acids and their condensation products with aromatic aldehydes", *Can. J. Chem.,* 1956, 34, 926–930.

Giaid et al., "Expression of endothelin–1 in lungs of patients with cryptogenic fibrosing alveolitis", *Lancet,* 1993, 341, 1550–1554.

Druml et al., "Endothelin–1 in Adult Respiratory Disease Syndrome", *Am. Rev. Respir. Dis.,* 1993, 148, 1169–1173.

Mitaka et al.,"Circulating Endothelin–1 Concentrations in Acute Respiratory Failure", *Chest,* 1993, 104, 476–480.

Kojima et al., "Plasma endothelin–1 like immunoreactivity levels in neonates", *Eur. J. Pediatr.,* 1992, 151, 913–915.

Sofia et al., "Increased 24–Hour Endothelin–1 Urinary Excretion in Patients with Chronic Obstructive Pulmonary Disease", *Respiration,* 1994, 61, 263–268.

Matthay et al., "Cardiovascular–Pulmonary Interaction in Chronic Obstructive Pulmonary Disease with Special Reference to the Pathogenesis and Management of Cor Pulmonale", *Obstructive Lung Disease,* 1990, 74:3, 571–618.

ENDOTHELIN ANTAGONISTS WITH ETHER-LINKED GROUPS

This application claims benefit of Provisional application Ser. No. 60/015,238 filed Apr. 10, 1996.

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, angina, arrhythmias, asthma, atherosclerosis, benign prostatic hyperplasia, Buerger's Disease, cardiac arrest, cardiogenic shock, cerebral trauma, Chrohn's Disease, congenital heart disease, congestive heart failure (CHF) (mild), congestive heart failure (CHF) (severe), cerebral ischemia, cerebral infarction, cerebral vasospasm, cirrhosis, diabetes, dilated cardiomyopathy, drowning (anoxia), endotoxic shock, gastric mucosal damage, glaucoma, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, male penile erectile dysfunction, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasu's arteritis, ulcerative colitis, uremia after hemodialysis, and uremia before hemodialysis.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include: ET-2, ET-3, vasoactive intestinal contractor (VIC), and the sarafotoxins (SRTXs).

The distribution of the two cloned receptor subtypes, termed $ET_A$ and $ET_B$, have been studied extensively (Arai H., et al., *Nature*, 1990;348:730, Sakurai T., et al., *Nature*, 1990;348:732). The $ET_A$, or vascular smooth muscle receptor, is widely distributed in cardiovascular tissues and in certain regions of the brain (Lin H. Y., et al., *Proc. Natl. Acad. Sci.*, 1991;88:3185). The $ET_B$ receptor, originally cloned from rat lung, has been found in rat cerebellum and in endothelial cells. The human ET receptor subtypes have been cloned and expressed (Sakamoto A., et al., *Biochem. Biphys. Res. Chem.*, 1991;178:656, Hosoda K., et al., *FEBS Lett.*, 1991;287:23). The $ET_A$ receptor clearly mediates vasoconstriction and there have been a few reports implicating the $ET_B$ receptor in the initial vasodilatory response to ET (Takayanagi R., et al., *FEBS Lett.*, 1991;282:103). However, recent data has shown that the $ET_B$ receptor can also mediate vasoconstriction in some tissue beds (Panek R. L., et al., *Biochem. Biophys. Res. Commun.*, 1992;183(2):566).

The involvement of endothelin has been proven in many human disease states.

Elevated levels of endothelin have been measured in patients suffering from ischemic heart disease (Yasuda M., et al., *Amer. Heart J.*, 1990;119:801–806) and either stable or unstable angina (Stewart J. T., et al., *Br. Heart J.*, 1991;66:7–9).

The degree of elevation of plasma ET levels in patients with heart failure varies from 2-fold to 5-fold (Stewart, et al., *Circulation*, 1992;85:510–517; Lerman, et al., *J. Am. Coll. Cardiology*, 1992;20: 849–853). The greatest elevation measured appears to be in congestive heart failure (CHF) patients with marked pulmonary hypertension. The increased level of circulating ET in human congestive heart failure patients also correlated with the severity of the disease observed (Rodeheffer, et al., *Am. J. Hypertension*, 1991:4:9A; Rodeheffer, et al., *Mayo Clin. Prod.*, 1992;67:719–724).

Many studies have indicated increased plasma levels of ET-1 after acute myocardial infarction (MI) in both animals and humans (Stewart, et al., *J. Am. Coll. Cardiol.*, 1991:18:38–43; Tomoda, et al., *Am. Heart J.*, 1993;125:667–672; Ray, et al., *Br. Heart J.*, 1992;67:383–386; Tsuji, et al., *Life Sci.*, 1991;48: 1745–1749). It has also been reported that the action of ET-1 may be enhanced under the conditions of ischemia (Liu, et al., *Biochem. Biophys. Res. Commun.*, 1989;164:1220–1225).

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of the infarction in a dose-dependent manner (Watanabe T., et al., "Endothelin in Myocardial Infarction," *Nature*, (Lond.) 1990;344:114). Thus, ET may be involved in the pathogenesis of congestive heart failure and myocardial ischemia (Margulies K. B., et al., "Increased Endothelin in Experimental Heart Failure," *Circulation*, 1990;82:2226).

Patients with chronic heart failure were treated with the ET antagonist Bosentan, which was found to improve cardiac performance, concluding that ET is involved in the regulation of vascular tone and that inhibition of its effects may be beneficial in chronic heart failure (Kiowski W., et al., Lancet, 1995;346: 732–36, also *J. Am. Coll Cardiol.*, 1995; special edition 296A:779-1).

Infusion of an endothelin antibody 1 hour prior to and 1 hour after a 60 minute period of renal ischaemia resulted in changes in renal function versus control. In addition, an increase in glomerular platelet-activating factor was attributed to endothelin (Lopez-Farre A., et al., *J. Physiology*, 1991;444: 513–522). In patients with chronic renal failure as well as in patients on regular hemodialysis treatment, mean plasma endothelin levels were significantly increased (Stockenhuber F., et al., *Clin. Sci. (Lond.)*, 1992;82:255–258).

Studies by Kon and colleagues using anti-ET antibodies in an ischemic kidney model, to deactivate endogenous ET, indicated the peptide's involvement in acute renal ischemic injury (Kon V., et al., "Glomerular Actions of Endothelin In Vivo," *J. Clin. Invest.*, 1989;83:1762).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno A., Effects of Endothelin-Specific Antibodies and Endothelin in Spontaneously Hypertensive Rats," *J. Tokyo Women's Med. Coll.*, 1991;61:951).

Other studies have demonstrated the usefulness of ET antagonists in maintaining beneficial parameters of renal performance following ischemia-induced injuries (Mino, et al., *Eur. J. Pharmacol.,* 1992;221:77–83; Benigni, et al., *Kidney Int.,* 1993;44:440–444).

$ET_A$ receptor MRNA has been detected in 82% of human meningiomas (*J. Clin. Invest.,* 1995;66:2017–2025 Plasma endothelin-1 levels were dramatically increased in a cancer patient with malignant hemangioendothelioma (Nakagawa K., et al., *Nippon Hifuka Gakkai Zasshi,* 1990; 100:1453–1456).

Exogenous endothelin-1 is also a prostate cancer mitrogen in vitro. Endothelin levels are significantly elevated in men with metastatic prostate cancer. Every human prostate cancer cell line tested by Nelson et al., (*Nature Medicine,* 1995;Vol 1(9):944) produced ET-1 MRNA and secreted immunoreactive endothelin.

An ET antagonist, PD 155080 was found to mediate prostate smooth muscle function in vivo, which demonstrated that endothelin antagonists may be useful in the treatment of benign prostatic hyperplasia (Chleko I., et al., Annual Meeting of the American Urological Assn, Orlando, 1996).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Respir. Dis.,* 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B. A., et al., *Am. J. Obstet. Gynecol.,* 1992;166:962–968).

Plasma immunoreactive endothelin-1 concentrations are elevated in patients with sepsis and correlate with the degree of illness and depression of cardiac output (Pittett J., et al., *Ann. Surg.,* 1991;213(3):262).

In addition, the ET-1 antagonist BQ-123 has been evaluated in a mouse model of endotoxic shock. This $ET_A$ antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry,* 1990;265(29):17432). In addition increased levels of plasma ET-1 have been observed in microalbuminuric insulin-dependent diabetes mellitus patients indicating a role for ET in endocrine disorders such as diabetes (Collier A., et al., *Diabetes Care,* 1992;15(8):1038).

Infusion of ET-1 produced a sustained, reversible, and salt-dependent hypertension when infused into normal, conscious rats (Mortensen, et al., *Hypertension,* 1990;15:720–723; Mortensen, et al., *FASEB J.,* 1991;5:A1105).

$ET_A$ antagonist receptor blockade has been found to produce an antihypertensive effect in normal to low renin models of hypertension with a time course similar to the inhibition of ET-1 pressor responses (Basil M. K., et al., *J. Hypertension,* 1992;10(Suppl. 4):S49). The endothelins have been shown to be arrhythmogenic, and to have positive chronotropic and inotropic effects, thus ET receptor blockade would be expected to be useful in arrhythmia and other cardiovascular disorders (Han S.-P., et al., *Life Sci.,* 1990;46:767).

Recently, an $ET_A$ selective antagonist demonstrated an oral antihypertensive effect (Stein P. D., et al., "The Discovery of Sulfonamide Endothelin Antagonists and the Development of the Orally Active $ET_A$ Antagonist 5-(Dimethylamino)-N-(3,4-dimethyl-5-isoxazolyl)-1-naphthalenesulfonamide," *J. Med. Chem.,* 1994;37: 329–331.

Plasma ET levels are elevated in patients with pulmonary hypertension (Yoshibayashi M., et al., *Circulation,* 1991;84:2280–2285). Increased expression has been measured indicating local production in the lung. Pulmonary hypertension is associated with the increased expression of endothelin-1 in vascular endothelial cells, suggesting that the local production of endothelin-1 may contribute to vascular abnormalities associated with pulmonary hypertension (Giaid A., et al., *N. Engl. J. Med.,* 1993;328:1732–9). In pulmonary hypertension, ET-1 is the most potent constrictor of airway smooth muscle thus far described in vitro (Pons, et al., *J. Pharmacol.,* 1991;102: 791–796). This response has been blocked by $ET_A$-receptor antagonists (Abraham, et al., *J. Appl. Physiol.,* 1993;74(5);2537–2542). Endothelin antagonists that block the production of endothelin and hence lower levels of endothelin have shown efficacy in several animal models of pulmonary hypertension. Pulmonary hypoxia increases ET-1 expression in the lung (*J. Sure. Res.,* 1994;57:280–283). For example, BQ-123, Bosentan, and PD 156707 provide protection in a rat hypoxia model of hypertension by lowering the increase in pulmonary vascular resistance and pulmonary arterial pressure (Eddahibi S., et al., *Am. J. Physiol.,* 1995;268:H828–835; Bonvallet S. T., et al., *Am. Rev. Rest. Dis.,* 1993;147:A493; IBC International Conference, R. Bialecki, Feb. 5, 1996, Coronado, Calif.). $ET_A$-receptor antagonists have been found to prevent and reverse chronic hypoxia-induced pulmonary hypertension in rat (DiCarlo, et al., *Am. J. Physiol.,* 1995;269:L690–L697; Chen, et al., *J. Appl. Physiol.,* 1995;79(6):2122–2131).

There is evidence that suggests the extent of increase in plasma ET-1 levels in patients with pulmonary hypertension may reflect the abnormalities of pulmonary circulation. It has been demonstrated that the pulmonary artery endothelial cells are injured in patients with congenital heart disease (Ishikawa S., et al., *J. Thorac. Cardiovasc. Sura.,* 1995; 110:271–3). Further, in cardiopulmonary bypass operations on patients with congenital heart disease, an immediate postoperative increase in circulating endothelin was observed which may predispose the patient to pulmonary vascular lability and crises in the postoperative period (Komai H., et al., *J. Thorac. Cardiovasc. Sura.,* 1993;106:473–8).

The widespread localization of the endothelins and their receptors in the central nervous system and cerebrovascular circulation has been described (Nikolov R. K., et al., *Drugs of Today,* 1992;28(5): 303–310). Intracerebroventricular administration of ET-1 in rats has been shown to evoke several behavioral effects. The potent vasoconstrictor action of ETs on isolated cerebral arterioles suggests the importance of these peptides in the regulation of cerebrovascular tone. These factors strongly suggest a role for the ETs in neurological disorders.

The volume of ischemic damage in the cerebral hemisphere of cats following middle cerebral artery occlusion was significantly reduced after the IV administration of PD 156707 (Patel, et al., *J. Cardiovasc. Pharmacol.,* 1995;26 (Suppl. 3):S412–S415). Reduction of ischemic brain injury in rats was also demonstrated following oral administration of the endothelin antagonist SB 217242 (Barone, et al., *J. Cardiovasc. Pharmacol.,* 1995;26(Suppl. 3): S404–S407).

Several studies have shown that endothelin levels are elevated in acute and chronic renal failure (Torralbo A., et al., *Am. J. Kid. Dis.*, 1995;25(16):918–923). Data in models of acute renal failure indicate that endothelin plays an important role. An endothelin receptor antagonist Bosentan that can block endothelin production and thereby lower levels has been reported to be effective in models of acute renal ischemia (Clozel M., et al., *Nature*, 1995;365:759). In dogs, the endothelin receptor antagonist SB 2090670 can attenuate ischemia-induced reductions in glomerular filtration rate and increases in fractional sodium excretion (Brooks D. P., et al, *J. Pharmacol. Exo. Ther.*, 1995). In addition, several antagonists have been shown to block radiocontrast-induced nephrotoxicity (Oldroyd S., et al., *Radiology*, 1995;196:661–665).

TAK-044 has shown protective effects in a model of acute renal failure in rats (*Life Sci.*, 1994;55(4): 301–310).

The $ET_A$ antagonist BQ-123 has been shown to prevent early cerebral vasospasm following subarachnoid hemorrhage (SAH) (Clozel M. and Watanabe H., *Life Sci.*, 1993;52:825–834; Lee K. S., et al., *Cerebral Vasoplasm*, 1993;217; and *Neurosurgery*, 1994;34:108). FR 139317 significantly inhibited the vasoconstriction of the basilar artery after 7 days in a canine two-hemorrhage model of SAH (Nirei H., et al., *Life Sci.*, 1993;52:1869). BQ-485 also significantly inhibited the vasoconstriction of the basilar artery after 7 days in a canine two-hemorrhage model of SAH (Yano, et al., *Biochem. Biophys. Res. Commun.*, 1993; 195:969). Ro 46-2005 (Clozel M., et al., *Nature*, 1993;365:759) has been shown to prevent early cerebral vasospasm following SAH in the rat with no significant effect on systemic arterial blood pressure. Treatment with Ro 47-0203=Bosentan (Clozel, et al., *Circulation*, 1993;88(4) part 2:0907) to rabbits with SAH had a 36±7% reduction of basilar artery cross-sectional area compared to sham rabbits. All of these studies show in vivo efficacy of endothelin antagonists in cerebral vasospasm resulting from SAH.

Circulating and tissue endothelin immunoreactivity is increased more than 2-fold in patients with advanced atherosclerosis (Lerman A., et al., *New England J. Med.*, 1991;325:997–1001). Increased endothelin immunoreactivity has also been associated with Buerger's disease (Kanno K., et al., *J Amer. Med. Assoc.*, 1990;264:2868) and Raynaud's phenomenon (Zamora M. R., et al., *Lancet*, 1990;336:1144–1147).

An increase of circulating endothelin levels was observed in patients that underwent percutaneous transluminal coronary angioplasty (PTCA) (Tahara A., et al., *Metab. Clin. Exp.*, 1991;40:1235–1237.

In an experiment to minimize restenosis following carotid artery balloon angioplasty in rats, the ET receptor antagonist SB 209670 was found to ameliorate neointima formation (Douglas, et al., *Circulation Res.*, 1994;75:190–197).

Local intra-arterial administration of endothelin has been shown to induce small intestinal mucosal damage in rats in a dose-dependent manner (Mirua S., et al., *Digestion*, 1991;48:163–172; Masuda E., et al., *Am. J. Physiol.*, 1992;262:G785–G790). Elevated endothelin levels have been observed in patients suffering from Crohn's disease and ulcerative colitis (Murch S. H., et al., *Lancet*, 1992;339:381–384).

The ET receptor antagonist bosentan was found to be an antagonist toward the ET-1-induced changes in gastric mucosal hemodynamics as well as on ET-1-induced gastric ulceration (Lazaratos, et al., *Pharmacol. Lett.*, 1995;56(9):195–200).

Graefe's *Arch. Clin. Ex. Ophthalmol*, 1995;233(8):484–488 provides data to support the hypothesis that vascular dysfunction may be involved in the pathogenesis of optic nerve damage in normal-tension glaucoma.

*Eur. J. Pharmacol.*, 1996;307(1):69–74 teaches a role for endothelins in penile erection.

Release of eicosanoids and endothelin in an experimental model of adult respiratory distress syndrome (ARDS) is covered in *Agents Actions Suppl., Prostaglandins Cardiovasc. Syst.*, 1992;37:41–6.

*Am. Rev. Respir. Dis.*, 1993;148:1169–1173 teaches venous ET-1 concentrations are massively increased in ARDS as a result of both increased formation and decreased clearance.

*Chest*, 1993;104:476–80 shows plasma ET-1 levels also positively correlate with right atrial pressure, systolic pulmonary arterial pressure, mean pulmonary arterial pressure, and resistance ratio (pulmonary vascular resistance/systemic vascular resistance) in ARDS.

In chronic obstructive pulmonary disease (COPD) and Cor Pulmonale associated with pulmonary hypertension patients excrete higher amounts of ET-1 compared to healthy subjects. Urinary ET-1 levels are further increased during acute exacerbation of the disease.

ET-1 levels in broncho alveolar lavage fluid from patients with COPD have been reported. ET-1 is involved in pulmonary endothelium damage caused by hypoxia in COPD patients. Pulmonary artery hypertension is the primary cardiovascular complication in COPD. (See Sofia, et al., *Respiration*, 1994:263–268(61); "Increased 24-Hour endothelin-1 urinary excretion in patients with chronic obstructive pulmonary disease" and Matthay, et al., *Medical Clinics of North America*, 1990:571–618(74); "Cardiovascular pulmonary interaction in chronic obstructive pulmonary disease with special reference to the pathogenesis and management of Cor Pulmonale."

ET-1 expression is increased in the lung vasculature of patients with pulmonary hypertension contributes to the medial hyperplasia and intimal fibrosis of cryptogenic fibrosing alveolitis. See Giaid, et al., *The Lancet*, 1993:1550–1554(341) Expression of endothelin-1 in lungs of patients with cryptogenic fibrosing alveolitis.

In summary, some of the conditions in which ET antagonists may be useful in treatment are as follows: acute respiratory distress syndrome (ARDS), angina, arrhythmias, asthma, atherosclerosis, benign prostatic hyperplasia, Buerger's Disease, cardiac arrest, cardiogenic shock, cerebral trauma, Chrohn's Disease, congenital heart disease, congestive heart failure (CHF) (mild), congestive heart failure (CHF) (severe), cerebral ischemia, cerebral infarction, cerebral vasospasm, chronic obstructive pulmonary diseases, cirrhosis, diabetes, dilated cardiomyopathy, drowning (anoxia), endotoxic shock, gastric mucosal damage, glaucoma, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, male penile erectile dysfunction, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasuls arteritis, ulcerative colitis, uremia after hemodialysis, and uremia before hemodialysis.

Allen C. F. H., Frame G. F., *Can. J. Research* 1932; 6:605 teaches the condensation of methyl and ethyl α-phenyl-β-

(para-substituted)benzoylpropionates with benzaldehyde and piperonal in the presence of sodium methylate, followed by acidification, produces cyclic compounds.

Allen C. F. H., Frame G. F., Normington J. B., Wilson C. V., *Can. J. Research* 1933;8:137 teaches the condensation of benzaldehyde with methyl and ethyl α-aryl-β-benzoylpropionates in the presence of sodium methylate, followed by acidification, to give unsaturated ketonic acids.

Allen, C. F., Normington, J. B., Wilson, C. V., *Can. J. Research* 1934;11:382 recites a number of highly substituted acrylic acids or their lactols.

Allen, C. F. H., Davis, T. J., Stewart, D. W., VanAllan, J. A., *Can. J. Chem.* 1956;34:926 shows that α aryl-β-aroylpropionic acids exist in an open-chain configuration while the condensation products of these latter acids with aromatic aldehydes are lactols, refuting his previous article *Can. J. Research* 1933;8:137.

Compounds of Formula

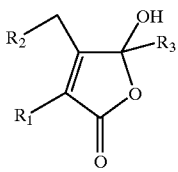

IA

| $R_1$ | $R_2$ | $R_3$ |
|---|---|---|
| phenyl | phenyl | phenyl |
| phenyl | phenyl | p-chloro-phenyl |
| phenyl | phenyl | p-bromophenyl |
| | phenyl | p-chloro-phenyl |
| piperonyl | | |
| phenyl | o-chlorophenyl | phenyl |
| phenyl | phenyl | p-phenyl-phenyl |
| anisyl (p-methoxyphenyl) | phenyl | phenyl |
| anisyl | α-furyl | phenyl |
| phenyl | piperonyl | p-chloro-phenyl |
| anisyl | o-chlorophenyl | phenyl |
| anisyl | o-methoxy-phenyl | phenyl |
| phenyl | phenyl | mesityl |
| phenyl | phenyl | p-methyl-phenyl |
| phenyl | o-chlorophenyl | p-chloro-phenyl |
| phenyl | phenyl | p-methoxy-phenyl |
| anisyl | o-methylphenyl | phenyl |
| phenyl | piperonyl | p-bromophenyl |
| phenyl | piperonyl | p-methoxy-phenyl | are all known from the above four literature references. However, the methods of using 2(5H)-furanone, 3-(1,3-benzodioxol-5-yl)-5-(4-chlorophenyl)-5-hydroxy-4-(phenylmethyl)- and a pharmaceutical composition containing it are new.

Copending U.S. application Ser. No. 08/384,083 covers nonpeptide endothelin antagonists of formula

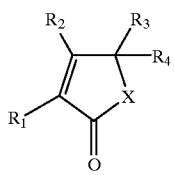

IB or a tautomeric open chain ketoacid form thereof or a pharmaceutically acceptable salt thereof wherein $R_1$ is cycloalkyl substituted or unsubstituted of from 3 to 12 carbon atoms,
   phenyl substituted with from 1 to 5 substituents, naphthyl unsubstituted or substituted with from 1 to 5 substituents, or
   heteroaryl unsubstituted or substituted with from 1 to 5 substituents;

$R_2$ is alkyl substituted or unsubstituted straight, or branched of from 1 to 12 carbon atoms,
   cycloalkyl substituted or unsubstituted of from 3 to 12 carbon atoms,
   aryl which is unsubstituted or substituted with from 1 to 5 substituents,
   heteroaryl which is unsubstituted or substituted with from 1 to 3 substituents;

$R_3$ is alkyl substituted or unsubstituted straight, or branched, of from 1 to 12 carbon atoms,
   cycloalkyl substituted or unsubstituted of from 3 to 12 carbon atoms,
   aryl which is unsubstituted or substituted with from 1 to 5 substituents,
   heteroaryl which is unsubstituted or substituted with from 1 to 3 substituents;

$R_4$ is hydroxy or $OR_5$
   $SR_5$, wherein $R_5$ is alkyl or substituted alkyl of from 1 to 7 carbon atoms, or
   $(CH_2)_n OR_5$ wherein n is an integer of from 1 to 3;

X is oxygen or sulphur;

with the proviso that when $R_1$ is monosubstituted phenyl and the substituent is p-methoxy, $R_3$ is not unsubstituted phenyl, monosubstituted phenyl, or mesityl and with the further proviso when $R_2$ is alkyl substituted, the substituent is not oxygen at the α-position to the furanone ring.

This application for patent is hereby incorporated by reference.

SUMMARY OF THE INVENTION

The instant invention is a compound of formula

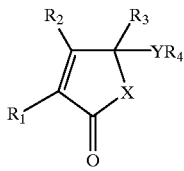

or a pharmaceutically acceptable salt thereof wherein
$R_1$ is cycloalkyl of from 3 to 12 carbon atoms substituted or unsubstituted,
  phenyl substituted with from 1 to 5 substituents,
  naphthyl unsubstituted or substituted with from 1 to 5 substituents, or
  heteroaryl unsubstituted or substituted with from 1 to 5 substituents;
$R_2$ is straight or branched alkyl of from 1 to 12 carbon atoms substituted or unsubstituted,
  cycloalkyl of from 3 to 12 carbon atoms substituted or unsubstituted,
  aryl unsubstituted or substituted with from 1 to 5 substituents, or
  heteroaryl unsubstituted or substituted with from 1 to 3 substituents;
$R_3$ is straight or branched alkyl of from 1 to 12 carbon atoms substituted or unsubstituted,
  cycloalkyl of from 3 to 12 carbon atoms substituted or unsubstituted,
  aryl which is unsubstituted or substituted with from 1 to 5 substituents, or
  heteroaryl unsubstituted or substituted with from 1 to 3 substituents;
$R_4$ is alkyl of from 1 to 7 carbon atoms, substituted with from 1 to 7 substituents, wherein one of the substituents is a group which enhances aqueous solubility. The solubility enhancing groups are selected from the secondary amino, tertiary amino, and sulfonic acid groups;
X and Y are each independently oxygen or sulfur; with the proviso that when $R_2$ is alkyl and is substituted, the substituent is not oxygen at the α-position to the furanone ring.

Preferred compounds of the instant invention are those of Formula I wherein
$R_1$ is phenyl substituted with from 1 to 5 substituents,
  naphthyl unsubstituted or substituted with from 1 to 5 substituents, or
  heteroaryl unsubstituted or substituted with from 1 to 5 substituents;
$R_2$ is straight or branched alkyl of from 1 to 7 carbon atoms substituted or unsubstituted;
$R_3$ is aryl substituted or unsubstituted or heteroaryl substituted or unsubstituted;

$R_4$ is alkyl of from I to 7 carbon atoms, substituted by 1 to 7 substituents, one of which is a group which enhances solubility and is selected from secondary amino, tertiary amino, and sulfonic acid;
X and Y are each independently oxygen or sulfur; with the proviso that when $R_2$ is alkyl and is substituted, the substituent is not oxygen at the α-position to the furanone ring.

More preferred compounds of the instant invention are those of Formula I wherein
$R_4$ is

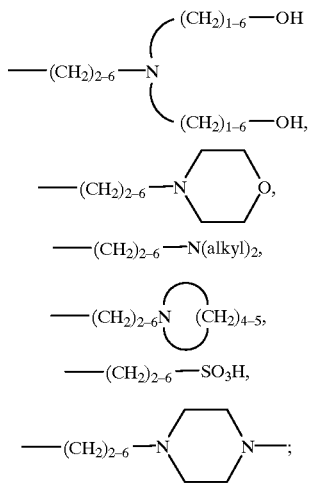

$R_2$ is benzyl,
  4-piperonylmethyl,
  3,4-dichlorobenzyl,
  3(N-Me)indolylmethyl,
  3,4-dimethoxybenzyl,
  2-aminobenzyl,
  3-aminobenzyl,
  4-aminobenzyl,
  2-hydroxybenzyl,
  3-hydroxybenzyl,
  4-hydroxybenzyl,
  3-Me$_2$aminobenzyl,
  4-Me$_2$aminobenzyl,
  3-Et$_2$aminobenzyl,
  4-Et$_2$aminobenzyl,
  4-isopropylbenzyl,
  4-chlorobenzyl,
  4-methoxybenzyl,
  4-methylbenzyl,
  3-methylbenzyl,
  4-isopropoxybenzyl,
  3-acetamidobenzyl,
  4-acetamidobenzyl,
  4-methylsulfonylbenzyl,
  3-methyl-4-methoxybenzyl,
  3-allyloxy-4-methoxybenzyl,
  3,4,5-trimethoxybenzyl,
  3-n-propoxybenzyl,
  3-carbethoxybenzyl
  4-carbethoxybenzyl,
  3-methoxybenzyl, or
  3-chlorobenzyl;
$R_3$ is 4-Me$_2$NPhenyl,
  3-methyl-4-methoxyphenyl,
  4-methoxyphenyl;

R₁ is 4-piperonyl, 3,5-dimethylphenyl, 3,5-dimethoxyphenyl, or 3-methoxy-4,5-methylenedioxyphenyl; and X and Y are oxygen.

Still more preferred compounds of the instant invention are selected from:

3-Benzo[1,3]dioxol-5-yl-5-(4-methoxy-phenyl)-5-(2-morpholin-4-yl-ethoxy)-4-(3,4,5-trimethoxy-benzyl)-5-(2-furan-2-one;

Sodium 3-[4-Benzo[1,3]dioxol-5-yl-2-(4-methoxy-phenyl)-5-oxo-3-(3,4,5-trimethoxy-benzyl)-2,5-phenyl)-5-oxo-3-(3,4,5-trimethoxy-benzyl)-2,5-dihydro-furan-2-yloxy]-propane-1-sulfonate;

3-Benzo[1,3]dioxol-5-yl-5-(3-dimethylamino-propxy)-5-(4-methoxy-phenyl)-4-(3,4,5-trimethoxy-benzyl)-5H-furan-2-one;

3-Benzo[1,3]dioxol-5-yl-5-(2-dimethylamino-ethoxy)-5-(4-methoxy-phenyl)-4-(3,4,5-trimethoxy-benzyl)-5H-furan-2-one;

3-(7-Methoxy-benzo[1,3]dioxol-5-yl)-5-(4-methoxy-phenyl)-5-(2-morpholin-4-yl-ethoxy)-4-(3,4,5-trimethoxy-benzyl)-5H-furan-2-one;

3-(3,5-Dimethoxy-phenyl)-5-(2-dimethylamino-ethoxy)-4-(3,4,5-trimethoxy-benzyl)-dihydrofuran-2-one;

3-Benzo[1,3]dioxol-5-yl-5-(4-methoxy-phenyl)-5-(pyrrolidin-2-ylmethoxy)-4-(3,4,5-trimethoxy-benzyl)-dihydrofuran-2-one;

3-Benzo[1,3]dioxol-5-yl-5-(4-methoxy-phenyl)-5-(2-pyrrolidin-1-yl-ethoxy)-4-(3,4,5-trimethoxy-benzyl)-dihydrofuran-2-one; and 3-Benzo[1,3]dioxol-5-yl-5-(4-methoxy-phenyl)-5-[2-(4-methyl-piperazin-1-yl)ethoxy]-4-(3,4,5-trimethoxy-benzyl)-dihydrofuran-2-one.

Elevated levels of endothelin have been shown to be involved in a number of pathophysiological states including angina, arrhythmias, asthma, atherosclerosis, benign prostatic hyperplasia, Buerger's Disease, cardiac arrest, cardiogenic shock, cerebral trauma, Chrohn's Disease, congenital heart disease, congestive heart failure (CHF) (mild), congestive heart failure (CHF) (severe), cerebral ischemia, cerebral infarction, cerebral vasospasm, cirrhosis, diabetes, dilated cardiomyopathy, drowning (anoxia), endotoxic shock, gastric mucosal damage, head injury, hemodialysis, hemorrhagic shock, hypertension (essential), hypertension (malignant), hypertension (pulmonary), hypertension (pulmonary, after bypass), hypoglycemia, inflammatory arthritides, ischemic bowel disease, ischemic disease, malignant hemangioendothelioma, myocardial infarction, myocardial ischemia, prenatal asphyxia, postoperative cardiac surgery, prostate cancer, preeclampsia, Raynaud's Phenomenon, renal failure (acute), renal failure (chronic), renal ischemia, restenosis, sepsis syndrome, subarachnoid hemorrhage (acute), surgical operations, status epilepticus, stroke (thromboembolic), stroke (hemorrhagic), Takayasu's arteritis, ulcerative colitis, uremia after hemodialysis, and uremia before hemodialysis. As antagonists of endothelin, the compounds of Formula I are useful in their treatment.

A still further embodiment of the present invention is a pharmaceutical composition for administering a therapeutically effective amount of a compound of Formula I in unit dosage form in the treatment methods mentioned above.

Finally, the present invention is directed to methods for production of a compound of Formula I.

DETAILED DESCRIPTION OF THE INVENTION

The solubilizing groups are selected from secondary or tertiary amino groups and sulfonic acids. The secondary amino groups are substituted by straight or branched chain alkyl, aryl, and heteroaryl, each of which can be either unsubstituted or substituted. The tertiary amino group has substituents independently selected from straight or branched alkyl which is unsubstituted or substituted by alkoxy, hydroxy, alkyl, amino, monosubstituted amino, disubstituted amino, and nitro. Other substituents are aryl and heteroaryl groups, each of which can be substituted or unsubstituted.

The substituents on the tertiary amino group can form a ring with the nitrogen into which they are attached, and may optionally contain additional heteroatoms such as N—R, O or S, such groups as morpholinyl, piperazinyl, and pyrrolidinyl. Preferred are the morpholinyl, piperazinyl, and 4-methyl piperazinyl solubilizing groups.

In the compounds of Formula I, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl. The alkyl group is unsubstituted or substituted by from 1 to 3 substituents selected from alkyl, alkoxy, thioalkoxy all as defined herein, hydroxy, thiol, nitro, halogen, amino, formyl, cycloalkyl, carboxyl, nitrile, monosubstituted amino, disubstituted amino,

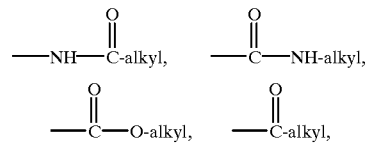

aryl, or heteroaryl wherein alkyl, aryl, and heteroaryl are defined as herein.

The term "cycloalkyl" means a saturated hydrocarbon ring which contains from 3 to 12 carbon atoms unless otherwise specified, for example, cyclopropyl, cyclobutyl, cyclopentyl, cyclohexyl, cycloheptyl, and adamantyl. The cycloalkyl ring may be unsubstituted or substituted by from 1 to 3 substituents selected from alkyl, cycloalkyl, cycloalkoxy, alkoxy, thioalkoxy all as defined herein, hydroxy, thiol, nitro, halogen, amino, monosubstituted amino, disubstituted amino, formyl, carboxyl, nitrile, alkylsulfoxyl, arylsulfoxyl, alkylsulfonyl, arylsulfonyl,

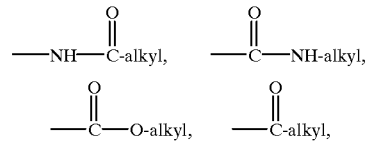

aryl, or heteroaryl wherein alkyl, aryl, and heteroaryl are defined as herein.

The terms "alkoxy" and "thioalkoxy" are O-alkyl or S-alkyl as defined above for alkyl.

Two alkoxy or thioalkoxy groups can be taken together to form a cyclic group such as

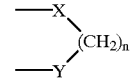

where X and Y are independently either O or S and n=1, 2, 3, or 4.

The term "aryl" means an aromatic radical which is a phenyl group, a benzyl group, a naphthyl group, a biphenyl group, a pyrenyl group, an anthracenyl group, or a fluorenyl group and the like, unsubstituted or substituted by 1 to 5 substituents selected from alkyl as defined above, alkoxy as defined above, thioalkoxy as defined above, hydroxy, thiol, nitro, halogen, amino, monosubstituted amino, disubstituted amino, formyl, carboxy, nitrile, arylsulfoxyl, alkylsulfoxyl, arylsulfonyl, alkylsulfonyl,

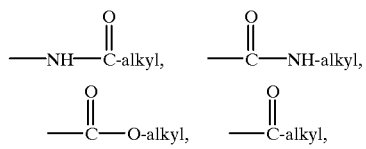

or heteroaryl wherein alkyl, aryl, and heteroaryl are defined as above.

The term "heteroaryl" means a heteroaromatic radical which is 2-or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-1,4-, or 5-pyridazinyl, 2-pyrazinyl, 2-, 4-, or 5-pyrimidinyl, 2-, 3-, 4-, 5-, 6-, 7-, or 8-quinolinyl, 1-1,3-, 4-, 5-, 6-, 7-, or 8-isoquinolinyl, 2-, 3-, 4-, 5-1,6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 3 substituents selected from alkyl as defined above, aryl as defined above, alkoxy as defined above, thioalkoxy as defined above, hydroxy, thiol, nitro, halogen, formyl, amino, monosubstituted mino, disubstituted amino, carboxyl, nitrile,

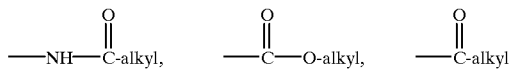

wherein alkyl is as defined above or phenyl.

"Halogen" is fluorine, chlorine, bromine, or iodine.

"Secondary amino" is defined by a nitrogen with two groups attached, $R_aNHR_b$.

"Tertiary amino" is defined by a nitrogen with three groups attached, $R_aNR_bR_c$.

The secondary and tertiary amino groups can occur as the immediate substitution or may be a substitution on any of the above defined groups.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, isethionic acid, and the like. Also contemplated are salts of amino acids such as arginate and the like and gluconate, galacturonate (see, for example, Berge S. M., et al., "Pharmaceutical Salts," *Journal of Pharmaceutical Science,* 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloro-procaine, choline, diethanolamine, dicyclohexylamine, ethylenediamine, N-methylglucamine, and procaine (see, for example, Berge S. M., et al., "Pharmaceutical Salts," *Journal of Pharmaceutical Science,* 1977; 66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of Formula I are valuable as antagonists of endothelin. The tests employed indicate that compounds of the invention possess endothelin antagonist activity. Thus, the compounds were tested for their ability to inhibit $[^{125}I]$-ET-1($[^{125}I]$-Endothelin-1) binding in a receptor assay. Compounds were also tested for antagonist activity by inhibition of ET-1 stimulated arachidonic acid release and ET-1 stimulated vasoconstriction.

The following radioligand binding assays were used (Reynolds E. E.; Keiser J. A.; Haleen S. J.; Walker D. M.; Davis L. S.; Olszewski B.; Taylor D. G.; Hwang O.; Welch K. M.; Flynn M. A.; Thompson D. M.; et. al., *J. Pharmacol. Exp. Ther.,* 1995;273:1410–1417).

The following cultured cells were used in binding experiments: CHO-KL cells expressing recombinant human $ET_BR$ (HERBA B), or Ltk- cells expressing human $ET_AR$ (HERBA A). Each of these cell types expressed a homogeneous population of the designated ET receptor subtype, which displayed canonical $ET_AR$ or $ET_BR$ pharmacology. Membranes were prepared from cultured cells by lysing cells in cold lysis buffer (5 mM HEPES, 2 mM EDTA, pH 7.4) and homogenizing with a Dounce "A" homogenizer. All of the homogenates were centrifuged at 30,000×g for 20 minutes at 4° C. Membrane pellets were resuspended in cold buffer containing 20 mM Tris, 2 nm EDTA, 200 $\mu$M Pefablock, 10 $\mu$M phosphoramidon, 10 $\mu$M leupeptin, and 1 $\mu$M pepstatin (pH 7.4) and frozen at −80° C. until use. Radioligand and competing ligands were prepared in binding buffer containing 20 mM Tris, 2 mM[] EDTA, and 0.1% BSA.

Competition binding assays were initiated by combining membranes, [$^{125}$]-ET-1 (40 pM) and competing ligand in a final volume of 250 μL and incubating for 2 hours at 37° C. The assay was terminated by filtration over Whatman GF/B filters that were presoaked with 50 mM Tris, pH 7.4, containing 0.2% BSA and 100 μM bacitracin. Nonspecific binding was defined as total binding minus nonspecific binding. Specific binding was analyzed by nonlinear least squared curve fitting (InPlot, GraphPad Software, San Diego, Calif.), and the estimated IC$_{50}$ value was used to calculate K$_i$ according to the method of Cheng and Prusoff (1973).

The following testing procedures were used (Doherty A M., et al., "Design of C-Terminal Peptide Antagonists of Endothelin: Structure-Activity Relationships of ET-1 [16–21, D-His$^{16}$]," *Bioorganic and Medicinal Chemistry Letters*, 1993;3:497–502).

Antagonist activity is measured by the ability of added compounds to reduce endothelin-stimulated arachidonic acid release in cultured vascular smooth muscle cells as arachidonic acid release (AAR). [$^{3}$H]Arachidonic Acid Loading Media (LM) is DME/F12+0.5% FCS×0.25 mCi/inL [$^{3}$] arachidonic acid (Amersham). Confluent monolayers of cultured rabbit renal artery vascular smooth muscle cells were incubated in 0.5 mL of the LM over 18 hours, at 37° C., in 5% CO$_2$. The LM was aspirated, and the cells were washed once with the assay buffer (Hank's BSS+10 mM HEPES+fatty acid-free BSA [1 mg/mL], and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 μL of the test compound (1 nM to 1 μM) and 10 μL ET-1 (0.3 nM), and the incubation was extended for 30 minutes. This solution was then collected, 10 μL of scintillation cocktail was added, and the amount of [$^{3}$H] arachidonic acid was determined in a liquid scintillation counter.

The data in Table 1 below shows the endothelin receptor binding and antagonists activity of representative compounds of the instant invention.

TABLE 1

| Example | HERBA-A[a] | HERBA-B[a] | AAR-A[b] |
| --- | --- | --- | --- |
| 1 | 2.8 | 12000 | 10 |
| 2 | 0.15 | 1900 | 0.3 |
| 3 | 12 | >2500 | NT[c] |
| 4 | 0.3 | 1080 | NT |
| 5 | 1.7 | 700 | NT |
| 6 | 2.6 | 2200 | NT |

[a]IC$_{50}$ values in nM
[b]Human cloned receptor data
[c]NT = Not tested.

As can be seen in Table 1 above, a representative compound of Formula I binds to the endothelin receptors ET$_A$ (HERBA-A) in the μM to nM range.

The said compounds also reduce endothelin-stimulated arachidonic acid release (AAR) and therefore are functional antagonists.

GENERAL SYNTHETIC APPROACHES

The compounds of Formula I may be prepared by at least two methods. In Scheme 1, an alpha-hydroxy butenolide is suspended or dissolved in a suitable inert solvent. The substituted alcohol HO-R$_4$ or mercapto compound HS-R$_4$ is added in excess, and an acidic catalyst is added. Typically, dichloromethane solvent may be used in the presence of anhydrous HCl gas to give the formation of the compound in Formula I.

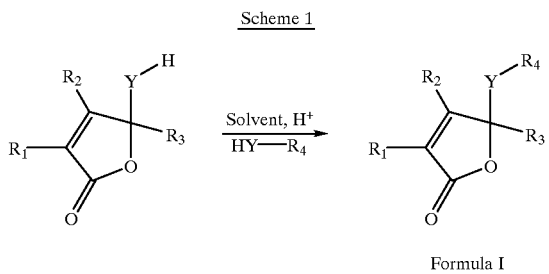

Scheme 1

Formula I

The compounds of Formula I may also be prepared by a second method. In Scheme 2, a butenolide with the alpha-ether substitution R$_5$ having a displacable group L is suspended or dissolved in a suitable inert solvent. The compound R$_6$ is added in excess, and L is displaced by R$_6$ to give a compound of Formula I. R$_5$ and R$_6$ are selected so as to combine to give an ether or thioether substitution, R$_4$, that is defined within the previous description of R$_4$.

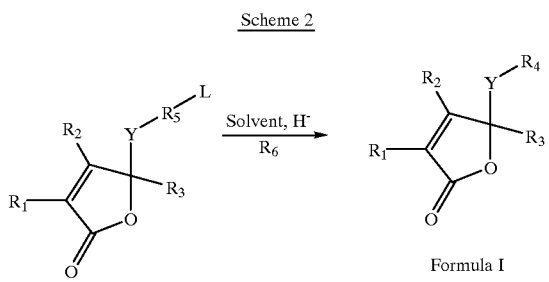

Scheme 2

Formula I

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the methods for preparing the compounds of the invention.

EXAMPLE 1

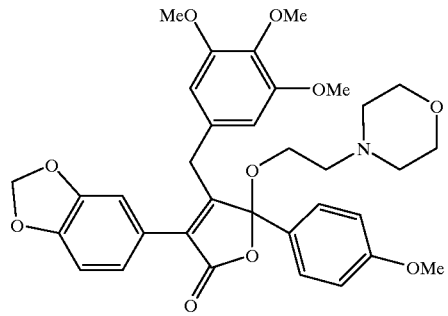

3-Benzo[1,3]dioxol-5-yl-5-(3-dimethylamino-propoxy)-5-(4-methoxy-phenyl)-4-(3,4,5-trimethoxy-benzyl)-5H-furan-2-one To 125 mL dichloromethane was added 3-Benzo[1,3]-dioxol-5-yl-5-hydroxy-5-(4-methoxy-phenyl)-4-(3,4,5-trimethoxy-benzyl)-5H-furan-2-one 6.06 g (11.96 mmol), giving a suspension. 4-(2-Hydroxyethyl)morpholine 3 g (22.86 imol) was added, and the mixture was purged with anhydrous HCl gas until saturated. After 3 hours at room temperature, additional 4-(2-hydroxyethyl)-morphline 3 g (22.86 mmol) was added, followed by stirring for 24 hours at room temperature. The mixture was evaporated in vacuo, and the residue was suspended in ethyl ether. The ether suspension was washed exhaustively with 4 N NaOH, followed by water and saturated sodium chloride solution. The ether phase was dried over anhydrous magnesium sulfate, filtered, and evaporated in vacuo to a crude foam, 2.86 g. The crude material was purified by chromatography on 200 g silica gel eluted with 5% methanol in chloroform. The appropriate fractions were evaporated to a glassy solid, 2.0 g. The product was identified by $^1$H NMR, MS [M—H]$^+$=620 Da.

INTERMEDIATE 1

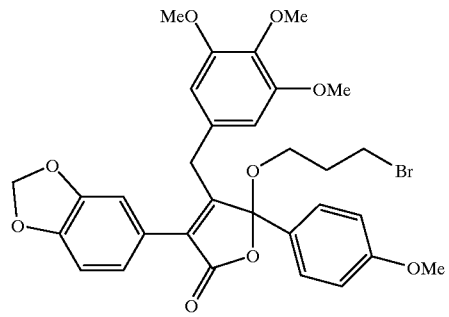

3-Benzo[1,3]dioxol-5-yl-5-(3-bromo-propoxy)-5-(4-methoxy-phenyl)-4-(3,4,5-trimethoxy-benzyl)-5H-furan-2-one To 100 mL dichloromethane was added 3-Benzo[1,3]-dioxol-5-yl-5-hydroxy-5-(4-methoxy-phenyl)-4-(3,4,5- trimethoxy-benzyl)-5H-furan-2-one 5.0 g (9.87 mmol), giving a suspension. 1-Bromo-3-propanol 3.07 g (22.15 mmol) was added, and the mixture was purged with anhydrous HCl gas until saturated. After 48 hours at room temperature, the mixture was evaporated in vacuo and the residue was suspended in ethyl ether. The ether suspension was washed exhaustively with 0.5 N NaOH, followed by water and saturated sodium chloride solution. The ether phase was dried over anhydrous magnesium sulfate, filtered, and diluted with hexane, giving a solid. Filter and dry in vacuo, giving a white solid, 4.79 g. The product was identified by $^1$H NMR, MS [M—H]$^+$=628, 629 Da.

EXAMPLE 2

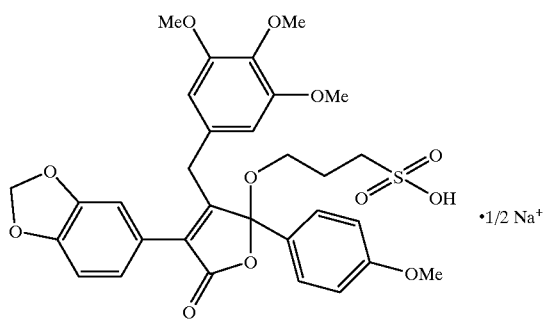

Sodium 3-[4-Benzo[1,3]dioxol-5-yl-2-(4-methoxy-phenyl)-5-oxo-3-(3,4,5-trimethoxy-benzyl)-2,5-dihydro-furan-2-yloxy]-propane-1-sulfonate To 50 mL 1,4-dioxane was added 3-Benzo[1,3]dioxol-5-yl-5-(3-bromo-propoxy)-5-(4-methoxy-phenyl)-4-(3,4,5-trimethoxy-benzyl)5H-furan-2-one 2.0 g (3.19 mmol). A solution of sodium sulfite, 0.88 g (7.0 mmol) in 50 mL water was added, and the mixture was refluxed for 18 hours. The mixture was evaporated in vacuo and the residue was suspended in ethyl ether and water. The suspension was acidified to pH 1 with 2 N HCl, giving an oily precipitate in the aqueous phase. The ether was decanted, and the oil was extracted into ethyl acetate and washed with saturated sodium chloride solution. The organic phase was dried over anhydrous magnesium sulfate, filtered, and diluted with ethyl ether, giving a solid. The solid was filtered and dried in vacuo, giving a white solid, 1.07 g. The product was identified by $^1$H NMR, MS [M—H]$^+$=627.3 Da. Elemental analysis indicated the material to contain ½ sodium salt per molecule.

EXAMPLE 3

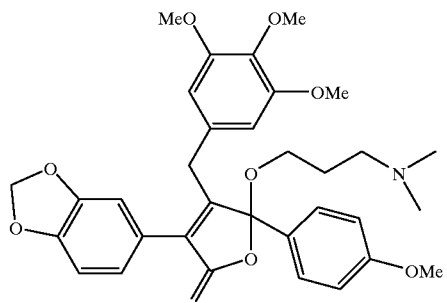

3-Benzo[1,3]dioxol-5-yl-5-(3-dimethylamino-propoxy)-5-(4-methoxy-phenyl)-4-(3,4,5-trimethoxy-benzyl)-5H-furan-2-one To 125 mL dichloromethane was added 3-Benzo[1,3]dioxol-5-yl-5-hydroxy-5-(4-methoxy-phenyl)-4-(3,4,5-trimethoxy-benzyl)-5H-furan-2-one 3.0 g (5.92 mmol), giving a suspension. N,N-dimethyl-propanolamine 2 g (19.4 mmol) was added, and the mixture was purged with anhydrous HCl gas until saturated. After an hour at room temperature, additional N,N-dimethylethanolamine 1 g (9.69 mmol) was added, followed by stirring for 24 hours at room temperature. The mixture was evaporated in vacuo and the residue was suspended in ethyl ether. The ether suspension was washed exhaustively with 4 N NaOH, followed by water and saturated sodium chloride solution. The ether phase was dried over anhydrous magnesium sulfate, filtered, and diluted with hexane, giving a solid. Filter and dry in vacuo, giving a white solid, 1.65 g. The product was identified by $^1$H NMR, MS [M—H]$^+$=592 Da.

EXAMPLE 4

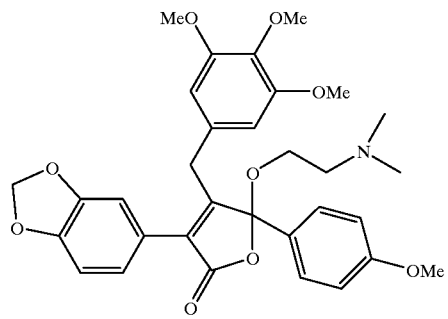

3-Benzo[1,3]dioxol-5-yl-5-(2-dimethylamino-ethoxy)-5-(4-methoxy-phenyl)-4-(3,4,5-trimethoxy-benzyl)-5H-furan-2-one To 125 mL dichloromethane was added 3-Benzo[1,3]dioxol-5-yl-5-hydroxy-5-(4-methoxy-phenyl)-4-(3,4,5-trimethoxy-benzyl)-5H-furan-2-one 6.06 g (11.96 mmol), giving a suspension. N,N-dimethyl-ethanolamine 4 g (44.9 mmol) was added, and the mixture was purged with anhydrous HCl gas until saturated. After an hour at room temperature, additional N,N-dimethylethanolamine 2 g (22.45 mmol) was added, followed by stirring for 48 hours at room temperature. The mixture was evaporated in vacuo and the residue was suspended in ethyl ether. The ether suspension was washed exhaustively with 4 N NaOH, followed by water and saturated sodium chloride solution. The ether phase was dried over anhydrous magnesium sulfate, filtered, and evaporated in vacuo to a crude foam, 2.86 g. The crude material was purified by chromatography on 200 g silica gel eluted with 5% methanol in chloroform. The appropriate fractions were evaporated to a glassy solid, 2.0 g. The product was identified by $^1$H NMR, MS [M—H]$^+$=578 Da.

EXAMPLE 5

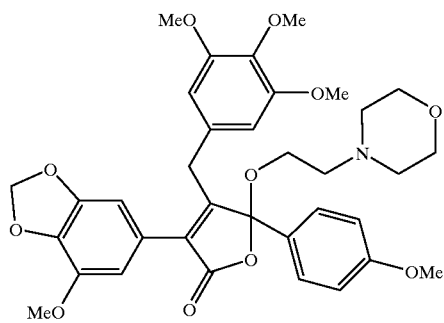

3-(7-Methoxy-benzo[1,3]dioxol-5-yl)-5-(4-methoxy-phenyl)-5-(2-morpholin-4-yl-ethoxy)-4-(3,4,5-trimethoxy-benzyl)-5H-furan-2-one To 125 mL dichloromethane was added 5-Hydroxy-3-(7-methoxy-benzo[1,3]dioxol-5-yl)-5-(4-methoxy-phenyl)-4-(3,4,5-trimethoxy-benzyl)-5H-furan-2-one 3.25 g (6.06 mmol), giving a suspension. 4-(2-Hydroxyethyl)morpholine 3.24 g (24.76 mmol) was added, and the mixture was purged with anhydrous HCl gas until saturated. After 24 hours at room temperature, the mixture was evaporated in vacuo and the residue was suspended in warm ethyl ether and water. Decant the aqueous phase and wash the ether phase with 1 N NaOH, followed by water and saturated sodium chloride solution. The ether phase was dried over anhydrous magnesium sulfate, filtered, and evaporated in vacuo to a glassy solid, 2.13 g. The product was identified by $^1$H NMR, MS [M—H]$^+$=650 Da.

EXAMPLE 6

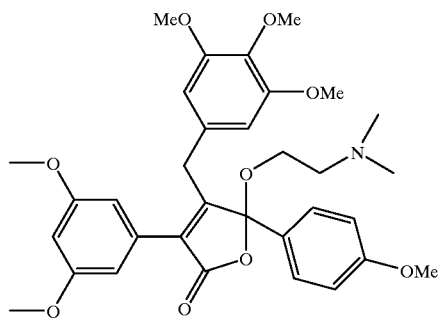

3-(3,5-Dimethoxy-phenyl)-5-(2-dimethylamino-ethoxy)-5-(4-methoxy-phenyl)-4-(3,4,5-trimethoxy-benzyl)-dihydro-furan-2-one To 125 mL dichloromethane was added 3-(3,5-Dimethoxy-phenyl)-5-hydroxy-5-(4-methoxy-phenyl)-4-(3,4,5-trimethoxy-benzyl)-5H-furan-2-one 5.0 g (9.57 mmol), giving a suspension. N,N-dimethylethanol-amine 2.66 g (29.8 mmol) was added, and the mixture was purged with anhydrous HCl gas until saturated. After an hour at room temperature, additional N,N-dimethyl-ethanolamine 1.33 g (14.9 mmol) was added, followed by stirring for 24 hours at room temperature. An additional N,N-dimethylethanolamine 2.66 g (29.8 mmol) was then added, followed by stirring for 24 hours at room temperature. The mixture was evaporated in vacuo, and the residue was suspended in ethyl ether. The ether suspension was washed exhaustively with 4 N NaOH, followed by water and saturated sodium chloride solution. The ether phase was dried over anhydrous magnesium sulfate, filtered, and evaporated in vacuo to a crude foam, 2.8 g. The crude material was purified by chromatography on 200 g silica gel eluted with 5% methanol in chloroform. The appropriate fractions were evaporated to a glassy solid, 2.31 g. The product was identified by $^1$H NMR, MS [M—H]$^+$=594.4 Da.

In a manner similar to that of Example 1, the following examples were prepared:

EXAMPLE 7

3-Benzo[1,3]dioxol-5-yl-5-(4-methoxy-phenyl)-5-(pyrrolidin-2-yl-methoxy)-4-(3,4,5-trimethoxy-benzyl)-dihydrofuran-2-one 5-(pyrrolidin-2-yl-methoxy)-4-(3,4,5-trimethoxy-benzyl)-dihydrofuran-2-one

EXAMPLE 8

3-Benzo[1,3]dioxol-5-yl-5-(4-methoxy-phenyl)-5-(2-pyrrolidin-1-yl-ethoxy)-4-(3,4,5-trimethoxy-benzyl)-dihydrofuran-2-one

EXAMPLE 9

3-Benzo[1,3]dioxol-5-yl-5-(4-methoxy-phenyl)-5-[2-(4-methyl-piperazin-1-yl)-ethoxy]-4-(3,4,5-trimethoxy-benzyl)-dihydrofuran-2-one

What is claimed is:

1. A compound of formula

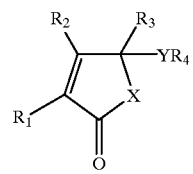

I or a pharmaceutically acceptable salt thereof wherein $R_1$ heteroaryl unsubstituted or substituted with from 1 to 5 substituents;

$R_2$ is straight or branched 1 of from 1 to 12 carbon atoms substituted or unsubstituted, cycloalkyl of from 3 to 12 carbon atoms substituted or unsubstituted, or aryl unsubstituted or substituted with from 1 to 5 substituents;

$R_3$ is straight or branched alkyl of from 1 to 12 carbon atoms substituted or unsubstituted, cycloalkyl of from 3 to 12 carbon atoms substituted or unsubstituted, or aryl which is unsubstituted or substituted with from 1 to 5 substituents;

$R_4$ is alkyl of from 1 to 7 carbon atoms, substituted by 1 to 7 substituents, one to four of which is a group which enhances aqueous solubility selected from the secondary amino, tertiary amino, and sulfonic acid groups;

X is oxygen;

Y is oxygen or sulfur;

with the proviso that when $R_2$ is all and is substituted, the substituent is not oxygen at the α-position to the furanone ring.

2. A compound according to claim 1 wherein $R_1$ is heteroaryl unsubstituted or substituted with from 1 to 5 substituents;

R₂ is straight or branched akyl of from 1 to 7 carbon atoms substituted or unsubstituted;

R₃ is aryl substituted or unsubstituted;

R₄ is alkyl of from 1 to 7 carbon atoms substituted by to 7substituents, one of which is a group which enhances solubility ad is selected from secondary amino, tertiary amino, and sulfonic acid;

X is oxygen;

Y is oxygen or sulfur;

with the proviso when R₂ is alkyl and is substituted, the substituent is not oxygen at the α-position to the furanone ring.

3. A compound according to claim 1 wherein R₄ is

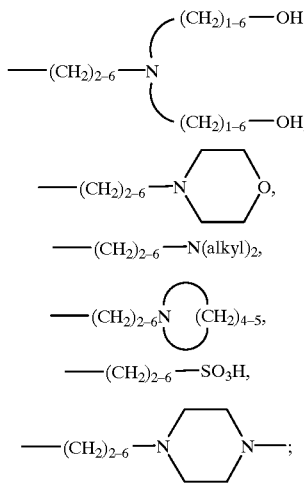

R₂ is benzyl,
3,4-dichlorobenzyl,
3,4-dimethoxybenzyl,
2-aminobenzyl,
3-aminobenzyl,
4-aminobenzyl,
2-hydroxybenzyl,
3-hydroxybenzyl,
4-hydroxybenzyl
3-Me₂aminobenzyl,
4-Me₂aminobenzyl,
3-Et₂aminobenzyl,
4-Et₂aminobenzyl,
4isopropylbenzyl,
4-chlorobenzyl,
4-methoxybenzyl,
4methylbenzyl,
3-methylbenzyl,
4isopropoxybenzyl,
3-acetamidobenzyl,
4-acetamidobenzyl,
4-methylsulfonylbenzyl,
3-methyl-4-methoxybenzyl,
3-allyloxy-4methoxybenzyl,
3,4,5-trimethoxybenzyl,
3-n-propoxybenzyl,
3-carbethoxybenzyl,
4-carbethoxybenzyl,
3-methoxybenzyl, or
3-chlorobenzyl;

R₃ is 4-Me₂NPh,
3-methyl-4-methoxyphenyl,
4-methoxyphenyl;

R₁ is 4-piperonyl, or
3-methoxy-4,5-methylenedioxyphenyl; and

X and Y are oxygen.

4. A compound according to claim 1 and selected from:

3-Benzo[1,3]dioxol-5-yl-5-(4-methoxy-phenyl)-5-(2-morpholin-4-yl-ethoxy)-4-(3,4,5-trimethoxy-benzyl)-5H-furan-2-one Sodium 3-[4-Benzo[1,3]dioxol-5-yl-2-(4-methoxy-phenyl)-5-oxo-3-(3,4,5-trimethoxy-benzyl)-2,5-dihydro-furan-2-yloxy]-propane-1-sulfonate;

3-Benzo[1,3]dioxol-5-yl-5-(3-dimethylamino-propoxy)-5-(4-methoxy-phenyl)-4-(3,4,5-trimethoxy-benzyl)-5H-furan-2-one;

3-Benzo[1,3]dioxol-5-yl-5-(2-dimethylamino-ethoxy)-5-(4-methoxy-phenyl)-4-(3,4,5-trimethoxy-benzyl)-5H-furan-2-one;

3-(7-Methoxy-benzo[1,3]dioxol-5-yl)-5-(4-methoxy-phenyl)-5-(2-morpholin-4-yl-ethoxy)-4-(3,4,5-trimethoxy-benzyl)-5H-furan-2-one;

3-(3,5-Dimethoxy-phenyl)-5-(2-dimethylamino-ethoxy)-5-(4-methoxy-phenyl)-4-(3,4,5-trimethoxy-benzyl)-dihydrofuran-2-one;

3-Benzo[1,3]dioxol-5-yl-5-(4-methoxy-phenyl)-5-(pyrrolidin-2-ylmethoxy)-4-(3,4,5-trimethoxy-benzyl)-dihydrofuran-2-one;

3-Benzo[1,3]dioxol-5-yl-5-(4-methoxy-phenyl)-5-(2-pyrrolidin-1-yl-ethoxy)-4-(3,4,5-trimethoxy-benzyl)-dihydrofuran-2-one; and 3-Benzo[1,3]dioxol-5-yl-5-(4-methoxy-phenyl)-5-[2-(4-methyl-piperazin-1-yl)-ethoxy]-4-(3,4,5-trimethoxy-benzyl)-dihydrofuran-2-one.

5. A pharmaceutical composition comprising a therapeutically effective amount of a compound according to claim 1 in admixture with a pharmaceutically acceptable excipient, diluent, and/or carrier.

6. A method of inhibiting elevated levels of endothelin comprising administering to a host suffering therefore a therapeutically effective amount of a composition according to claim 1 in unit dosing form.

7. A method of treating all vascular diseases, comprising administering to a host suffering therefrom a therapeutically effective amount of a compound according to claim 1 in unit dosage form.

8. A method of treating mild or severe congestive heart failure comprising administering to a host suffering therefrom a therapeutically effective amount of a compound according to claim 1 in unit dosage form.

9. A method of treating cerebral ischemia, cerebral infarction, or embolic stroke, comprising administering to a host suffering therefrom a therapeutically effective amount of a compound according to claim 1 in unit dosage form.

10. A method of treating cerebral vasospasm, subarachnoid hemorrhage or hemorrhagic stroke comprising administering to a host suffering therefrom a therapeutically effective amount of a compound according to claim 1 in unit dosage form.

11. A method of treating diabetes comprising administering to a host suffering therefrom a therapeutically effective amount of a compound according to claim 1 in unit dosage form.

12. A method of treating gastric ulceration and mucosal damage, ischemic bowel disease, or Chrohn's disease comprising administering to a host suffering therefrom a therapeutically effective amount of a compound according to claim 1 in unit dosage form.

13. A method of treating essential and malignant hypertension comprising administering to a host suffering therefrom a therapeutically effective amount of a compound according to claim 1 in unit dosage form.

14. A method of treating pulmonary hypertension or pulmonary hypertension after bypass surgery comprising administering to a host suffering therefrom a therapeutically effective amount of a compound according to claim 1 in unit dosage form.

15. A method of treating myocardial infarction or ischemia comprising administering to a host suffering therefrom a therapeutically effective amount of a compound according to claim 1 in unit dosage form.

16. A method of treating acute or chronic renal failure, renal ischemia, or radiocontrast-induced nephrotoxicity comprising administering to a host suffering therefrom a therapeutically effective amount of a compound according to claim 1 in unit dosage form.

17. A method of treating endotoxic, septic or hemorrhagic shock comprising administering to a host suffering therefrom a therapeutically effective amount of a compound according to claim 1 in unit dosage form.

18. A method of treating angina comprising administering to a host suffering therefrom a therapeutically effective amount of a compound according to claim 1 in unit dosage form.

19. A method of treating preeclampsia comprising administering to a host suffering therefrom a therapeutically effective amount of a compound according to claim 1 in unit dosage form.

20. A method of treating asthma comprising administering to a host suffering therefrom a therapeutically effective amount of a compound according to claim 1 in unit dosage form.

21. A method of treating arrhythmias comprising administering to a host suffering therefrom a therapeutically effective amount of a compound according to claim 1 in unit dosage form.

22. A method of treating benign prostatic hyperplasia comprising administering to a host suffering therefrom a therapeutically effective amount of a compound according to claim 1 in unit dosage form.

23. A method of treating glaucoma comprising administering to a host suffering therefrom a therapeutically effective amount of a compound according to claim 1 in unit dosage form.

24. A method of treating male penile erectile dysfunction comprising administering to a host suffering therefrom a therapeutically effective amount of a compound according to claim 1 in unit dosage form.

25. A method of treating acute respiratory distress syndrome (ARDS) comprising administering to a host suffering therefrom a therapeutically effective amount of a compound according to claim 1 in unit dosage form.

26. A method of treating chronic obstructive pulmonary diseases comprising administering to a host suffering therefrom a therapeutically effective amount of a compound according to claim 1 in unit dosage form.

27. A method of treating cryptogenic fibrosing alveolitis comprising administering to a host suffering therefrom a therapeutically effective amount of a compound according to claim 1 in unit dosage form.

28. A process by analogy for the preparation of a compound of Formula I above which is an ether-linked endothelin antagonist useful in disease states associated with elevated levels of endothelin which comprises:

(1) suspending or dissolving an a-hydroxy butenolide in a suitable inert solvent;

(2) adding in excess a substituted alcohol HO-$R_4$ or mercapto compound HS-$R_4$ and an acidic catalyst to produce a compound of Formula I

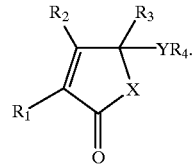

29. A process by analogy for the preparation of a compound of Formula I above which is an ether-linked endothelin antagonist useful in disease states associated with elevated levels of endothelin which comprises:

(1) suspending or dissolving in a suitable inert solvent a compound of Formula

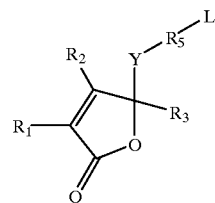

wherein $R_5$ is an alkyl group of 1 to 7 carbons and L is a displacable group, (2) adding an excess of $R_6$ which is a solubilizing group selected from secondary amino, tertiary amino or sulfonic acid and displacing L to produce a compound of Formula I, where $R_5$ and $R_6$ form a group of $R_4$ described earlier.

30. A method of treating atherosclerosis, restenosis, or Raynaud's phenomenon comprising administering to a host suffering therefrom a therapeutically effective amount of a compound according to claim 1 in unit dosage form.

* * * * *